United States Patent [19]
Theriot

[11] Patent Number: 5,917,091
[45] Date of Patent: Jun. 29, 1999

[54] PREPARATION AND USE OF 2-METHYL-5-PHENYLISOXAZOLIDINE

[75] Inventor: Kevin J. Theriot, Baton Rouge, La.

[73] Assignee: Albemarle Corporation, Richmond, Va.

[21] Appl. No.: 09/046,931

[22] Filed: Mar. 23, 1998

Related U.S. Application Data

[62] Division of application No. 08/901,235, Jul. 25, 1997, Pat. No. 5,760,243.
[51] Int. Cl.$^6$ .................................................. C07C 213/08
[52] U.S. Cl. ............................................ 564/347; 564/355
[58] Field of Search ...................... 564/347, 355

[56] References Cited

FOREIGN PATENT DOCUMENTS

| 0162383 | 11/1985 | European Pat. Off. . |
| 0272555 | 6/1988 | European Pat. Off. . |
| 0273265 | 7/1988 | European Pat. Off. . |

OTHER PUBLICATIONS

Fornefeld et al., "Cycloaddition Reaction With Methylnitrone", J. Org. Chem., 1979, vol. 44, No. 5, pp. 835–839.

*Primary Examiner*—Joseph K. McKane
*Attorney, Agent, or Firm*—Philip M. Pippenger

[57] ABSTRACT

(a) An alkali metal base (hydroxide, oxide, carbonate, bicarbonate or sesquicarbonate), an acid addition salt of N-methylhydroxylamine, and (iii) water are mixed together to form a reaction mixture in which the acid of the acid addition salt has been neutralized. (b) Reaction mixture from (a) and formaldehyde or formalin are mixed together and the resultant mixture is subjected to reaction conditions that produce a reaction mixture in which N-methylnitrone has been formed. (c) Reaction mixture from (b) and styrene are mixed and the resultant mixture to subjected to reaction conditions that produce a reaction mixture in which 2-methyl-5-phenylisoxazolidine has been formed. Preferably, 2-methyl-5-phenylisoxazolidine formed in (c) is hydrogenated such that N-methyl-3-phenyl-3-hydroxypropylamine is formed, which in turn is reacted with 4-halobenzotrifluoride such that N-methyl-3-phenyl-3-[4-trifluoromethyl)phenoxy]propylamine is formed. Conversion of the N-methyl-3-phenyl-3-[4-trifluoromethyl)phenoxy]propylamine to its racemic hydrochloride salt provides fluoxetine hydrochloride, a widely used antidepressant.

10 Claims, No Drawings

PREPARATION AND USE OF 2-METHYL-5-PHENYLISOXAZOLIDINE

This is a Division of commonly-owned U.S. application Ser. No. 08/901,235, filed Jul. 25, 1997, now U.S. Pat. No. 5,760,243, issued Jun. 2, 1998.

2-Methyl-5-phenylisoxazolidine is a useful intermediate in the synthesis of N-methyl-3-phenyl-3-[4-trifluoromethyl) phenoxy]propylamine and acid addition salts thereof, such as the racemic hydrochloride salt known generically as fluoxetine hydrochloride, a widely used antidepressant.

In accordance with an embodiment of this invention, 2-methyl-5-phenylisoxazolidine is produced by:

a) mixing together, concurrently or in any sequence, ingredients which comprise (I) at least one water-soluble alkali metal hydroxide, oxide, carbonate and/or bicarbonate (ii) at least one acid addition salt of N-methylhydroxylamine, and (iii) water, to form a reaction mixture in which the acid of the acid addition salt(s) has/have been neutralized;

b) mixing together reaction mixture from a) and formaldehyde or formalin, and subjecting the resultant mixture to reaction conditions effective to form a reaction mixture in which N-methylnitrone has been formed; and c) mixing together reaction mixture from b) and styrene, and subjecting the resultant mixture to reaction conditions effective to produce a reaction mixture in which 2-methyl-5-phenylisoxazolidine has been formed.

Steps a), b), and c) can be, and preferably are, conducted in the same reaction vessel. Moreover, it is not necessary to isolate intermediates formed in this process sequence. Thus in b) formaldehyde or formalin can be mixed with (preferably, added to) the entire product mixture formed in a), and likewise in c) styrene can be mixed with (preferably, added to) the entire product mixture formed in b). If desired, portions of the reaction products from a) or b), or from both a) and b), can be separated and used for other purposes, and in such case only a portion of the reaction product of a) and/or b) (as the case may be) would be used in the ensuing reaction of b) and/or c) (as the case may be).

Another advantage of the process of this invention is that when properly performed, the process enables formation of 2-methyl-5-phenylisoxazolidine in high yields.

E. J. Fornefeld and A. J. Pike, *J. Org. Chem.* 1979, 44, No. 5, 835–9, describe the preparation of 3-methyl-5-substituted isoxazolidines by vigorously stirring a mixture of a dipolarophile, sodium acetate trihydrate, 37% aqueous formaldehyde in ethanol or dioxane at room temperature during the dropwise addition of a solution of N-methylhydroxylamine hydrochloride in ethanol or dioxane containing a small amount of water. After stirring for 3 hours or allowing the mixture to stand overnight, the sodium chloride is removed by filtration. Then the filtrate is concentrated somewhat under reduced pressure, diluted with an equal volume of water, neutralized with sodium bicarbonate, and extracted with ethyl acetate. The extract is dried, and concentrated under reduced pressure. Unfortunately, the use of sodium acetate results in the formation of acetic acid which can act to hydrolyze the nitrone intermediate, a drawback which is not experienced when employing aqueous alkali metal hydroxide solution (which of course can be formed from an alkali metal hydroxide or oxide) or aqueous alkali metal carbonate or bicarbonate solution pursuant to this invention. Also the process of this invention is facilitated by neutralizing the acid addition salt of N-methylhydroxylamine with the aqueous alkali metal hydroxide, carbonate, or bicarbonate solution before mixing with the styrene (a dipolarophile).

Thus the above process of this invention is deemed to constitute a highly advantageous, novel contribution to the art.

Step a)

In step a) of the process of this invention, the base used is one or more water-soluble alkali metal oxides and/or hydroxides and/or carbonates and/or bicarbonates and/or sesquicarbonates. Preferably, these compounds are sodium or potassium compounds, or any combination of any of these. Use of NaOH is convenient and usually is the most economical base for use in this step. However the water soluble oxides, hydroxides, carbonates, bicarbonates and/or sesquicarbonates of the other alkali metals (Li, Rb, Cs) can be used, if desired, either separately or in any combination with or without conjoint use of one or more oxides and/or hydroxides and/or carbonates and/or bicarbonates and/or sesquicarbonates of sodium and/or potassium. Also, the foregoing basic substances that form hydrates can be used in the form of a hydrate. For convenience, these alkali metal substances, whether used individually or in a combination of two or more of them, are sometimes collectively referred to hereinafter as "alkali metal base".

By the term "water-soluble" is meant that the initial alkali metal compound (hydroxide, oxide, carbonate, bicarbonate or sesquicarbonate) is sufficiently soluble in water at ambient room temperature to form a solution of sufficient concentration to enable the solution to be used in neutralizing the acid of the acid addition salt(s) of N-methylhydroxylamine without requiring use of an excessively large volume of such aqueous solution relative to the quantity of the acid addition salt being used. As a rule of thumb, the alkali metal hydroxides, oxides, carbonates, bicarbonates and sesquicarbonates that have a water solubility at least equivalent to that of lithium bicarbonate (about 5.5 grams per 100 milliliters at 13° C.) can be used and in general, the higher the solubility above this level, the better.

The acid addition salt or salts of N-methylhydroxylamine can be a hydrohalide, sulfate, phosphate, carbonate, or the like. The preferred acid addition salt is the hydrochloride, but the hydrobromide, hydroiodide, sulfate, phosphate, carbonate, or any combination (or mixture) of any two or more of these with or without the hydrochloride salt can be used. For convenience, these acid addition salts, whether used individually or in a combination of two or more of them, are sometimes collectively referred to hereinafter as "N-methylhydroxylamine salt".

A sufficient amount of water is used to form a clear solution from the N-methylhydroxylamine salt and the alkali metal base used. At least a stoichiometric amount of the alkali metal base should be used relative to the N-methylhydroxylamine salt in order to completely neutralize the salt-forming acid of the N-methylhydroxylamine salt. In general, use of from 1 to about 1.05 equivalents of alkali metal base per equivalent the N-methylhydroxylamine salt is recommended.

This neutralization reaction is typically conducted at one or more temperatures in the range of about 0 to about 100° C., and since the reaction tends to be an exothermic reaction it is helpful to control the temperature by suitable control of the rate of mixing, by use of precooled water, and/or by cooling the reaction mixture during the reaction itself.

One or more ancillary organic solvents can be used, if desired. These include 1,4-dioxane, methanol, ethanol, propanol, isopropyl alcohol, tetrahydrofuran, and other like inert materials which form homogeneous solutions with water under the conditions to be used in the reaction.

Step b)

Formaldehyde or formalin is mixed with all or a portion of the reaction mixture from step a) so that N-methylnitrone is formed. Typically the amounts of these reactants are proportioned to provide in the range of about 0.9 to about 1.05 moles of formaldehyde per mole of N-methylhydroxylamine in the quantity of the reaction mixture from step a) being used.

Typically this nitrone formation reaction is conducted at one or more temperatures in the range of about 0 to about 50° C. Because this is an exothermic reaction, it is helpful to control the temperature such as by suitable control of the rate of mixing, by use of precooled formalin and/or pre-cooled reaction mixture from a), and/or by cooling the reaction mixture during the reaction itself.

The amount of water (and ancillary organic solvent such as referred to above in connection with step a), if any is used) should be sufficient to provide a liquid phase reaction mixture.

Step c)

In this step, all or a portion of the reaction mixture from step b) is mixed with styrene, and the resultant mixture is subjected to reaction conditions effective to produce a reaction mixture in which 2-methyl-5-phenylisoxazolidine has been formed. Preferably this is accomplished by maintaining the mixture in a sealed reaction vessel to at least one temperature in the range of about 20 to about 120° C. under autogenous pressure for a period in the range of about 1 to about 24 hours such that 2-methyl-5-phenylisoxazolidine is formed.

The reaction involves one mole of styrene per mole of N-methylnitrone and thus if either reactant is present in less than a stoichiometric amount, it becomes the limiting reactant. Typically the amount of styrene used in forming the reaction mixture will fall in the range of about 0.9 to about 1.1 moles per mole of N-methylnitrone present in the quantity of the reaction mixture from b) being used. It is desirable to stir or otherwise agitate the reaction mixture during at least a substantial portion of the reaction period.

When desired, recovery of 2-methyl-5-phenylisoxazolidine from the reaction mixture from c) can be effected in various ways. One convenient procedure comprises mixing a base such as sodium carbonate or dilute aqueous NaOH with the reaction mixture from c); extracting the basified mixture with a suitable relatively volatile organic solvent such as chloroform, diethyl ether, toluene, or the like; drying the organic phase with a suitable solid state, neutral or basic water absorbent such as potassium carbonate, sodium carbonate, sodium sulfate, or the like; removing the absorbent such as by filtration, centrifugation, decantation, or like procedure; and stripping off the organic solvent under suitable temperature and pressure conditions.

Examples 1 and 2, wherein percentages are by weight unless otherwise specified, illustrate the practice and advantages of the above embodiment of this invention, and are not to be construed as constituting limitations on the invention.

EXAMPLE 1

N-methylnitrone: Sodium hydroxide (4.8 g, 120 mmol) was dissolved in p-dioxane/water (21 g/9 g). N-Methylhydroxylamine hydrochloride (10.0 g. 120 mmol) was added with cooling. Formalin (10.0 g, 120 mmol) was added with cooling to form a reaction mixture containing N-methylnitrone.

2-Methyl-5-phenylisoxazolidine: Styrene (11.3 g. 109 mmol) was added to the foregoing reaction mixture, and the reactor was sealed and heated to 125° C. for 24 hours. The reaction mixture was cooled and analyzed by GC which showed 95 area % conversion of styrene and 92 area % of 2-methyl-5-phenylisoxazolidine. The mixture was basified with 5% aqueous NaOH, and extracted with $CHCl_3$. The $CHCl_3$ phase was dried ($K_2CO_3$), filtered, and stripped to give (15.8 g, 89%) 2-methyl-5-phenylisoxazolidine.

EXAMPLE 2

N-methylnitrone: Sodium hydroxide (4.8 g, 120 mmol) was dissolved in water (30 g). N-Methylhydroxylamine hydrochloride (10.0 g, 120 mmol) was added with cooling. Formalin (10.0 g, 120 mmol) was added with cooling whereby N-methylnitrone was formed in the reaction mixture.

2-Methyl-5-phenylisoxazolidine: Styrene (11.3 g, 109 mmol) was added to the reaction mixture, and the reactor was sealed and heated to 130° C. for 19 hours. The reaction mixture was cooled and analyzed by GC which showed 94% conversion of styrene and 87% 2-methyl-5-phenylisoxazolidine.

Other embodiments of this invention include: (I) processes for the preparation of N-methyl-3-phenyl-3-hydroxypropylamine that can be used in the preparation of N-methyl-3-phenyl-3-[4-trifluoromethyl)phenoxy] propylamine and acid addition salts thereof, and (ii) processes for the preparation of N-methyl-3-phenyl-3-[4-trifluoromethyl)phenoxy]propylamine and acid addition salts thereof. These embodiments will now be considered seriatim.

Preparation of N-methyl-3-phenyl-3-hydroxypropylamine

In this embodiment 2-methyl-5-phenylisoxazolidine formed in c) is subjected to hydrogenation such that N-methyl-3-phenyl-3-hydroxypropylamine is formed. N-methyl-3-phenyl-3-hydroxypropylamine is a highly useful intermediate for the synthesis of N-methyl-3-phenyl-3-[4-trifluoromethyl)phenoxy]propylamine and acid addition salts thereof. The hydrogenation can be effected by in situ generation of hydrogen, for example by use of finely divided zinc and aqueous acetic acid. Preferably, however, the hydrogenation is effected catalytically by use of hydrogen and a suitable catalyst such as palladium on carbon.

When generating the hydrogen in situ, a mixture consisting essentially of 2-methyl-5-phenylisoxazolidine, water, acetic acid and finely-divided zinc is maintained at one or more temperatures in the range of about 50 to about 100° C. for a sufficient period of time for N-methyl-3-phenyl-3-hydroxypropylamine to be formed in an appropriate yield (e.g., at least 80%). Usually periods in the range of about 1 to about 12 hours will suffice. The amount of acetic acid and finely-divided zinc should be sufficient to generate at least 15% excess hydrogen over the stoichiometric amount required for the reaction.

The catalytic hydrogenation preferably uses 5% or 10% palladium on carbon as catalyst and hydrogen pressures in the range of about 10 to about 100 psig at temperatures in the range of about 20 to about 80° C. However, other suitable hydrogenation catalysts may be used. The reaction should be conducted under essentially anhydrous conditions and thus at least substantially all of the water present in the reaction mixture from c) should be separated or removed, e.g., by a phase cut between the organic and aqueous phases, preferably followed by drying using a suitable solid state, neutral or basic, water absorbent such as potassium carbonate, sodium carbonate, sodium sulfate, or the like. Effective catalytic quantities of palladium-carbon catalyst are typically in the range of about 0.1 to about 5.0 wt % of the weight of the 2-methyl-5-phenylisoxazolidine be used in the reaction. Reaction periods in the range of 2 to about 24 are typical, with the lower temperatures and pressures usually requiring the longer reaction periods, and vice versa. Completion of the reaction is indicated by cessation of hydrogen uptake.

Examples 3–6 serve to illustrate ways by which 2-methyl-5-phenylisoxazolidine can be converted into N-methyl-3-phenyl-3-hydroxypropylamine by means of a suitable hydrogenation step.

EXAMPLE 3

2-Methyl-5-phenylisoxazolidine (2.0 g, 12.3 mmol) and Zn powder (1.2 g, 18.3 mmol) in 10 molar aqueous acetic acid are heated to 65–70° C. for 4 hours. Additional Zn powder (0.4 g, 6.1 mmol) is added and heating is continued for one more hour. The reaction mixture is neutralized with sodium hydroxide and extracted with chloroform. The extract is dried ($K_2CO_3$) and concentrated to give N-methyl-3-phenyl-3-hydroxypropylamine.

EXAMPLE 4

2-Methyl-5-phenylisoxazolidine (12.6 g, 77.3 mmol) in EtOH (134 g) is mixed with 5% Pd/C (1.2 g) in a glass pressure reactor. The reactor is warmed to 40–50° C. and the pressure maintained at 40 psig with $H_2$ until the pressure becomes constant (ca. 24 hours). The mixture is filtered through Celite and the solvent is removed to give N-methyl-3-phenyl-3-hydroxypropylamine.

EXAMPLE 5

2-Methyl-5-phenylisoxazolidine (38.1 g, 234 mmol) dissolved in tetramethylene sulfone (38.1 g) is mixed with 5% Pd/C (1.9 g) in a glass pressure reactor. The reactor is warmed to 50° C. and the pressure is maintained at 40 psig with $H_2$ for 24 hours. Ethanol (38.1 g) is added and heating is continued for 48 hours. After cooling, the mixture is filtered and the EtOH is removed to give a solution of N-methyl-3-phenyl-3-hydroxypropylamine in tetramethylene sulfone.

EXAMPLE 6

2-Methyl-5-phenylisoxazolidine (54.3 g, 333 mmol) and Pd/C (2.7 g) in EtOH (55.0 g) are heated to 60–80° C. in a 300-mL, stirred (700 rpm), Hastalloy autoclave which is kept pressurized to 55 psig with $H_2$ for 5 hours. After cooling, the mixture is filtered and the EtOH removed in vacuo to give N-methyl-3-phenyl-3-hydroxypropylamine.

Preparation of N-methyl-3-phenyl-3-[4-(trifluoromethyl) phenoxy]propylamine

This embodiment of the present invention comprises conducting steps a), b), and c) above, converting 2-methyl-5-phenylisoxazolidine from step c) to N-methyl-3-phenyl-3-hydroxypropylamine via a hydrogenation step such as described above, and then reacting N-methyl-3-phenyl-3-hydroxypropylamine so formed with a 4-halobenzotrifluoride to form N-methyl-3-phenyl-3-[4-(trifluoromethyl)phenoxy]propylamine. The 4-halobenzotrifluoride used in the last step of this sequence is preferably 4-fluorobenzotrifluoride or 4-chlorobenzotrifluoride. However, 4-bromobenzotrifluoride or 4-iodobenzotrifluoride, or combinations (or mixtures) of any two, three, or of all four of these 4-halobenzotrifluorides can be used.

The reaction involves one mole of the 4-halobenzotrifluoride per mole of the N-methyl-3-phenyl-3-hydroxypropylamine. Therefore either reactant can be present in excess and the other becomes the limiting reactant. Typically the proportions of these reactants will be in the range of about 1 to about 2 moles of the 4-halobenzotrifluoride per mole of the N-methyl-3-phenyl-3-hydroxypropylamine. The reaction is best performed in a polar aprotic solvent such as sulfolane, N-methylpyrrolidinone, N,N-dimethylformamide, N,N-diethylformamide, N,N-dimethylacetamide, dimethylsulfoxide, or the like, to which a strong base in a finely-divided solid state, such as NaOH or KOH, has been added in an amount in the range of about 1.1 to about 1.5 moles per mole of N-methyl-3-phenyl-3-hydroxypropylamine used. A phase transfer catalyst such as tetrabutylammonium bromide, cetyltrimethylammonium chloride, tetrabutylammonium hydrogen sulfate, or the like can also be employed in amounts in the range of about 0.1 to about 5.0 based on N-methyl-3-phenyl-3-hydroxypropylamine, if desired.

Typically, the reaction is performed at one or more temperatures in the range of about 80 to about 150° C. Reaction periods are typically within the range of about 1 to about 24 hours. Upon completion of the reaction, it is desirable to add water to the mixture and to extract the solution with a suitable solvent such as ethyl ether or methylene chloride which is then washed with water until essentially all of the polar aprotic solvent is removed. Alternatively, the polar aprotic solvent can be removed by distillation, followed by a similar solvent extraction work up. The product is recovered by removal of the solvent, for example by distillation at reduced pressure. The N-methyl-3-phenyl-3-[4-trifluoromethyl)phenoxy]propylamine can be converted to acid addition salts thereof by conventional procedures. For example, racemic fluoxetine can be formed by treating racemic N-methyl-3-phenyl-3-[4-trifluoromethyl)phenoxy]propylamine with anhydrous hydrogen chloride followed by low temperature crystallization (e.g., in the range of about 0 to about 30° C.) of the racemic fluoxetine from toluene solution.

Examples 7–9 serve to illustrate ways by which N-methyl-3-phenyl-3-[4-trifluoromethyl)phenoxy] propylamine can be formed by reaction between N-methyl-3-phenyl-3-hydroxypropylamine and 4-chlorobenzotrifluoride.

EXAMPLE 7

N-Methyl-3-phenyl-3-hydroxypropylamine (10.7 g, 64.8 mmol), 4-chlorobenzotrifluoride (13.0 g, 72.0 mmol), and NaOH (5.5 g, 138 mmol) are dissolved in N-methylpyrrolidinone (100 g), and the solution is heated to 130° C. for 24 hours. After cooling, water (200 mL) is added and the solution is extracted with ether (2×100 mL). The combined ether extracts are washed with water (6×50 mL), dried ($K_2CO_3$) and the solvent is removed in vacuo to give N-methyl-3-phenyl-3-[4-trifluoromethyl)phenoxy] propylamine as a brown oil. The oil is dissolved in toluene (150 mL) and anhydrous HCl is bubbled through the solution until saturated. Upon cooling to 0° C., crystallization occurs to give fluoxetine hydrochloride as a gray solid. The fluoxetine hydrochloride can be further purified by recrystallization from ethyl acetate/cyclohexane.

EXAMPLE 8

N-Methyl-3-phenyl-3-hydroxypropylamine (49.8 g, 302 mmol), 4-chlorobenzotrifluoride (60.0 g, 332 mmol), powdered 87% KOH (22.0 g, 341 mmol), and tetrabutylammonium hydrogen sulfate (0.5 g, 1.5 mmol) and sulfolane (47 g) are combined and heated to 150° C. under a nitrogen condenser for 24 hours. More 4-chlorobenzotrifluoride (11.0 g, 61 mmol) and KOH (3.0 g, 47 mmol) are added and heating is continued for 48 hours. After cooling, water (300 mL) is added, and the aqueous solution is extracted with ether (3×100 mL) and the combined extracts are washed with water (2×100 mL). The ether solution is dried ($K_2CO_3$). The ether is removed in vacuo and the product is distilled (125–130° C., 0.5 mm Hg) to give N-methyl-3-phenyl-3-[4-trifluoromethyl)phenoxy]propylamine.

EXAMPLE 9

Powdered KOH (87%, 14.4 g, 257 mmol) is added to a mixture of N-methyl-3-phenyl-3-hydroxypropylamine (30.8 g, 187 mmol) and 4-chlorobenzotrifluoride (40.0 g, 221 mmol) in N-methylpyrrolidinone (100.0 g). The mixture is heated to 130° C. for 17 hours. The temperature is then raised to 150° C. and more KOH (6.5 g, 116 mmol) is added. Heating is continued for an additional 24 hours. More 4-chlorobenzotrifluoride (10.0 g, 55 mmol) is added and heating is continued for 10 hours. After cooling, water (200 mL) is added and the solution is extracted with $CH_2Cl_2$ (3×100 mL). The extract is washed with water (2×100 mL), dried $K_2CO_3$, and the solvent is removed in vacuo. The crude product is distilled (125–130° C., 0.5 mm Hg) to give N-methyl-3-phenyl-3-[4-trifluoromethyl)phenoxy]propylamine.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. In short, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, formed in situ, blended or mixed with one or more other substances, components and/or ingredients in accordance with the present disclosure. Thus the fact that a substance, component or ingredient may have lost its original identity through a chemical reaction or transformation during the course of contacting, in situ formation, blending or mixing operations, (such as, for example, ionization, solvation, complex formation, or any other chemical interaction or physical change) if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises:
   a) mixing together concurrently or in any sequence ingredients which comprise (i) at least one alkali metal base selected from water-soluble alkali metal oxides, hydroxides, carbonates, bicarbonates, and sesquicarbonates, (ii) at least one acid addition salt of N-methylhydroxylamine, and (iii) water, to form a reaction mixture in which the acid of the acid addition salt has been neutralized;
   b) mixing together reaction mixture from a) and formaldehyde or formalin and subjecting the resultant mixture to reaction conditions effective to form a reaction mixture in which N-methylnitrone has been formed;
   c) mixing together reaction mixture from b) and styrene and subjecting the resultant mixture to reaction conditions effective to produce a reaction mixture in which 2-methyl-5-phenylisoxazolidine has been formed; and
   d) subjecting 2-methyl-5-phenylisoxazolidine formed in c) to hydrogenation such that N-methyl-3-phenyl-3-hydroxypropylamine is formed.

2. A process according to claim 1 wherein in a) the acid addition salt of N-methylhydroxylamine is N-methylhydroxylamine hydrohalide; wherein the N-methylhydroxy-lamine hydrohalide is added to (i) a preformed aqueous sodium hydroxide solution, or (ii) a preformed aqueous potassium hydroxide solution, or (iii) a preformed aqueous sodium hydroxide and potassium hydroxide solution; wherein in b) formalin is added to reaction mixture from a); wherein in c) the styrene is added to reaction mixture from b); and wherein the hydrogenation in d) is catalytic hydrogenation using hydrogen and a palladium-carbon catalyst.

3. A process according to claim 1 wherein the acid addition salt of N-methylhydroxylamine is N-methylhydroxylamine hydrochloride, and wherein at least a), b), and c) are conducted in the same reaction vessel.

4. A process according to claim 1 wherein said acid addition salt of N-methyl-3-phenyl-3-[4-trifluoromethyl)phenoxy]propylamine is formed by reaction of hydrogen chloride with said N-methyl-3-phenyl-3-[4-trifluoromethyl)phenoxy]propylamine.

5. A process which comprises:
   a) mixing together concurrently or in any sequence ingredients which comprise (i) at least one alkali metal base selected from water-soluble alkali metal oxides, hydroxides, carbonates, bicarbonates, and sesquicarbonates, (ii) at least one acid addition salt of N-methylhydroxylamine, and (iii) water, to form a reaction mixture in which the acid of the acid addition salt has been neutralized;
   b) mixing together reaction mixture from a) and formaldehyde or formalin and subjecting the resultant mixture to reaction conditions effective to form a reaction mixture in which N-methylnitrone has been formed;
   c) mixing together reaction mixture from b) and styrene and subjecting the resultant mixture to reaction conditions effective to produce a reaction mixture in which 2-methyl-5-phenylisoxazolidine has been formed;
   d) subjecting 2-methyl-5-phenylisoxazolidine formed in c) to hydrogenation such that N-methyl-3-phenyl-3-hydroxypropylamine is formed; and e) reacting N-methyl-3-phenyl-3-hydroxypropylamine from d) with 4-halobenzotrifluoride such that N-methyl-3-phenyl-3-[4-trifluoromethyl)phenoxy] propylamine is formed.

6. A process according to claim 5 wherein in a) the acid addition salt of N-methylhydroxylamine is an N-methylhydroxylamine hydrohalide; wherein the N-methylhydroxylamine hydrohalide is added to (i) a preformed aqueous sodium hydroxide solution, or (ii) a preformed aqueous potassium hydroxide solution, or (iii) a preformed aqueous sodium hydroxide and potassium hydroxide solution; wherein in b) formalin is added to reaction mixture from a); wherein in c) the styrene is added to reaction mixture from b); wherein the hydrogenation in d) is catalytic hydrogenation using hydrogen and a palladium-carbon catalyst; and wherein in e) the 4-halobenzotrifluoride is 4-chlorobenzotrifluoride.

7. A process according to claim 6 wherein in a) the acid addition salt of N-methylhydroxylamine is N-methylhydroxylamine hydrochloride, and wherein in c) said resultant reaction mixture is heated in a sealed reaction vessel to at least one temperature in the range of about 20 to about 120° C. under autogenous pressure for a period in the range of about 1 to about 24 hours.

8. A process according to claim 7 further comprising forming a hydrochloride salt of N-methyl-3-phenyl-3-[4-trifluoromethyl)phenoxy]propylamine formed in e).

9. A process according to claim 5 wherein in a) the acid addition salt of N-methylhydroxylamine is N-methylhydroxylamine hydrochloride, and wherein at least a), b), and c) are conducted in the same reaction vessel.

10. A process according to claim 5 further comprising forming an acid addition salt of N-methyl-3-phenyl-3-[4-trifluoromethyl)phenoxy]propylamine formed in e).

* * * * *